(12) United States Patent
Hart

(10) Patent No.: US 8,496,705 B2
(45) Date of Patent: Jul. 30, 2013

(54) METHOD OF ANCHORING AUTOLOGOUS OR ARTIFICIAL TENDON GRAFTS IN BONE

(75) Inventor: Rickey D. Hart, North Attleboro, MA (US)

(73) Assignee: DePuy Mitek, LLCR, Raynham, MA (US)

(*) Notice: Subject to any disclaimer, the term of this patent is extended or adjusted under 35 U.S.C. 154(b) by 0 days.

(21) Appl. No.: 13/311,320

(22) Filed: Dec. 5, 2011

(65) Prior Publication Data

US 2012/0078369 A1 Mar. 29, 2012

Related U.S. Application Data

(60) Division of application No. 12/617,392, filed on Nov. 12, 2009, now Pat. No. 8,100,969, which is a division of application No. 10/623,212, filed on Jul. 18, 2003, now Pat. No. 7,637,949, which is a division of application No. 08/976,257, filed on Nov. 21, 1997, now Pat. No. 6,616,694, and a continuation-in-part of application No. 08/887,580, filed on Jul. 3, 1997, now abandoned, which is a continuation-in-part of application No. 08/754,566, filed on Nov. 21, 1996, now abandoned.

(51) Int. Cl.
*A61F 2/08* (2006.01)

(52) U.S. Cl.
USPC ............... 623/13.14; 623/13.12; 623/13.13

(58) Field of Classification Search
USPC ............................. 623/13.11–13.19
See application file for complete search history.

(56) References Cited

U.S. PATENT DOCUMENTS

| 2,381,050 A | 12/1943 | Hardinge |
| 3,036,482 A | 9/1960 | Kenworthy |
| 3,525,365 A | 8/1970 | Meulendyk et al. |
| 3,566,739 A | 3/1971 | Lebar |
| 3,708,883 A | 1/1973 | Flander |
| 3,842,824 A | 10/1974 | Neufeld |
| 3,896,500 A * | 7/1975 | Rambert et al. ............ 623/13.14 |
| 3,953,896 A * | 5/1976 | Treace ........................ 623/13.12 |
| 4,013,071 A | 3/1977 | Rosenberg |
| 4,091,806 A | 5/1978 | Aginsky |
| 4,400,833 A | 8/1983 | Kurland |

(Continued)

FOREIGN PATENT DOCUMENTS

| CA | 2142017 A1 | 12/1994 |
| CA | 2272251 A1 | 5/1998 |

(Continued)

OTHER PUBLICATIONS

EP Search Report Jul. 28, 2008, for application EP 03078619.

*Primary Examiner* — Paul Prebilic

(57) ABSTRACT

An anchor assembly for autologous or artificial tendon grafts comprises an insertion element and a stabilizing element. The insertion element has a stem and a head containing an aperture large enough to receive a graft. The stabilizing element is adapted to be embedded in bone, and comprises a sleeve with a cavity arranged to receive and hold the insertion element stem. In use, the stabilizing element is affixed in the bone, and the stem of the insertion element is placed therein. A tendon graft may be secured to the insertion element either before or after its placement in the stabilizing element. Two such anchors may be linked with one or multiple grafts, in either a two-ply or four-ply arrangement.

12 Claims, 10 Drawing Sheets

U.S. PATENT DOCUMENTS

| | | | |
|---|---|---|---|
| 4,408,938 A | 10/1983 | Maguire | |
| 4,467,478 A | 8/1984 | Jurgutis | |
| 4,484,570 A | 11/1984 | Sutter et al. | |
| 4,492,226 A | 1/1985 | Belykh et al. | |
| 4,506,670 A | 3/1985 | Crossley | |
| 4,590,928 A | 5/1986 | Hunt et al. | |
| 4,605,414 A | 8/1986 | Czajka | |
| 4,632,100 A | 12/1986 | Somers et al. | |
| 4,708,132 A | 11/1987 | Silvestrini | |
| 4,712,542 A | 12/1987 | Daniel et al. | |
| 4,716,893 A | 1/1988 | Fischer et al. | |
| 4,738,255 A | 4/1988 | Goble et al. | |
| 4,741,330 A | 5/1988 | Hayhurst | |
| 4,744,793 A | 5/1988 | Parr et al. | |
| 4,759,765 A * | 7/1988 | Van Kampen | 623/13.14 |
| 4,778,468 A | 10/1988 | Hunt et al. | |
| 4,828,562 A | 5/1989 | Kenna | |
| 4,870,957 A * | 10/1989 | Goble et al. | 623/13.12 |
| 4,871,289 A | 10/1989 | Choiniere | |
| 4,873,976 A | 10/1989 | Schreiber | |
| 4,901,711 A | 2/1990 | Goble et al. | |
| 4,927,421 A | 5/1990 | Goble et al. | |
| 4,940,467 A | 7/1990 | Tronzo | |
| 4,944,742 A | 7/1990 | Clemow et al. | |
| 4,988,351 A | 1/1991 | Paulos et al. | |
| 4,998,233 A | 3/1991 | DiMatteo et al. | |
| 5,002,578 A | 3/1991 | Luman | |
| 5,013,316 A | 5/1991 | Goble et al. | |
| 5,037,422 A | 8/1991 | Hayhurst et al. | |
| 5,046,513 A | 9/1991 | Gatturna et al. | |
| 5,059,206 A | 10/1991 | Winters | |
| 5,062,843 A | 11/1991 | Mahony, III | |
| 5,084,050 A | 1/1992 | Draenert | |
| 5,102,421 A | 4/1992 | Anspach, Jr. | |
| 5,108,433 A | 4/1992 | May et al. | |
| 5,116,337 A | 5/1992 | Johnson | |
| 5,116,373 A | 5/1992 | Jakob et al. | |
| 5,129,902 A | 7/1992 | Goble et al. | |
| 5,141,373 A | 8/1992 | Kendall | |
| 5,141,520 A | 8/1992 | Goble et al. | |
| 5,151,104 A | 9/1992 | Kenna | |
| 5,152,763 A | 10/1992 | Johnson | |
| 5,152,790 A | 10/1992 | Rosenberg et al. | |
| 5,169,400 A | 12/1992 | Muhling et al. | |
| 5,176,682 A | 1/1993 | Chow | |
| 5,207,679 A | 5/1993 | Li | |
| 5,209,753 A | 5/1993 | Biedermann et al. | |
| RE34,293 E | 6/1993 | Goble et al. | |
| 5,224,946 A | 7/1993 | Hayhurst et al. | |
| 5,226,766 A | 7/1993 | Lasner | |
| 5,234,434 A | 8/1993 | Goble et al. | |
| 5,236,445 A | 8/1993 | Hayhurst et al. | |
| 5,248,231 A | 9/1993 | Denham et al. | |
| 5,258,015 A | 11/1993 | Li et al. | |
| 5,266,075 A * | 11/1993 | Clark et al. | 606/138 |
| 5,268,001 A | 12/1993 | Nicholson et al. | |
| 5,314,429 A | 5/1994 | Goble | |
| 5,324,308 A | 6/1994 | Pierce | |
| 5,326,205 A | 7/1994 | Anspach, Jr. et al. | |
| 5,350,380 A | 9/1994 | Goble et al. | |
| RE34,762 E | 10/1994 | Goble et al. | |
| 5,352,229 A | 10/1994 | Goble et al. | |
| 5,354,298 A | 10/1994 | Lee et al. | |
| 5,354,300 A | 10/1994 | Goble et al. | |
| 5,372,604 A | 12/1994 | Trott | |
| 5,385,567 A | 1/1995 | Goble | |
| 5,393,302 A | 2/1995 | Clark et al. | |
| RE34,871 E | 3/1995 | McGuire et al. | |
| 5,397,356 A | 3/1995 | Goble et al. | |
| 5,403,320 A | 4/1995 | Luman et al. | |
| 5,411,523 A | 5/1995 | Goble | |
| 5,417,692 A | 5/1995 | Goble et al. | |
| 5,417,712 A | 5/1995 | Whittaker et al. | |
| 5,425,490 A | 6/1995 | Goble et al. | |
| 5,425,767 A | 6/1995 | Steininger et al. | |
| 5,431,651 A | 7/1995 | Goble | |
| 5,443,482 A | 8/1995 | Stone et al. | |
| 5,458,601 A | 10/1995 | Young, Jr. et al. | |
| 5,464,427 A | 11/1995 | Curtis et al. | |
| 5,472,452 A | 12/1995 | Trott | |
| 5,480,403 A | 1/1996 | Lee et al. | |
| 5,486,197 A | 1/1996 | Le et al. | |
| 5,489,210 A | 2/1996 | Hanosh | |
| 5,496,326 A | 3/1996 | Johnson | |
| 5,500,001 A | 3/1996 | Trott | |
| 5,501,683 A | 3/1996 | Trott | |
| 5,501,695 A | 3/1996 | Anspach, Jr. et al. | |
| D368,777 S | 4/1996 | Goble et al. | |
| 5,505,735 A | 4/1996 | Li | |
| 5,522,845 A | 6/1996 | Wenstrom, Jr. | |
| 5,545,108 A | 8/1996 | Wagner et al. | |
| 5,545,180 A | 8/1996 | Le et al. | |
| D374,286 S | 10/1996 | Goble et al. | |
| D374,287 S | 10/1996 | Goble et al. | |
| D374,482 S | 10/1996 | Goble et al. | |
| 5,562,671 A | 10/1996 | Goble et al. | |
| 5,569,252 A | 10/1996 | Justin et al. | |
| 5,571,104 A | 11/1996 | Li | |
| 5,632,748 A | 5/1997 | Beck, Jr. et al. | |
| 5,645,568 A | 7/1997 | Chervitz et al. | |
| 5,665,110 A | 9/1997 | Chervitz et al. | |
| 5,681,289 A | 10/1997 | Wilcox et al. | |
| 5,688,284 A | 11/1997 | Chervitz et al. | |
| 5,697,933 A | 12/1997 | Gundlapalli et al. | |
| 5,702,397 A | 12/1997 | Goble et al. | |
| 5,707,395 A * | 1/1998 | Li | 606/232 |
| 5,725,529 A | 3/1998 | Nicholson et al. | |
| 5,730,744 A | 3/1998 | Justin et al. | |
| 5,759,184 A | 6/1998 | Santangelo | |
| 5,766,250 A | 6/1998 | Chervitz et al. | |
| 5,782,918 A | 7/1998 | Klardie et al. | |
| 5,871,504 A | 2/1999 | Eaton et al. | |
| 5,888,218 A | 3/1999 | Folsom | |
| 5,902,321 A | 5/1999 | Caspari et al. | |
| 5,911,721 A | 6/1999 | Nicholson et al. | |
| 5,931,840 A | 8/1999 | Goble et al. | |
| 5,935,129 A | 8/1999 | McDevitt et al. | |
| 5,968,044 A * | 10/1999 | Nicholson et al. | 606/232 |
| 6,562,071 B2 * | 5/2003 | Jarvinen | 623/13.14 |
| 6,616,694 B1 * | 9/2003 | Hart | 623/13.14 |
| 6,887,271 B2 | 5/2005 | Justin et al. | |
| 7,008,451 B2 | 3/2006 | Justin et al. | |
| 7,306,626 B2 | 12/2007 | Whelan | |
| 7,637,949 B2 * | 12/2009 | Hart | 623/13.14 |
| 8,100,969 B2 * | 1/2012 | Hart | 623/13.14 |
| 2006/0095131 A1 | 5/2006 | Justin et al. | |

FOREIGN PATENT DOCUMENTS

| | | |
|---|---|---|
| DE | 3406961 A1 | 9/1985 |
| DE | 8520206 U1 | 12/1985 |
| DE | 3601865 | 1/1987 |
| EP | 0058744 A1 | 9/1982 |
| EP | 0124489 A1 | 11/1984 |
| EP | 0232049 A1 | 8/1987 |
| EP | 0238223 | 9/1987 |
| EP | 0241240 A2 | 10/1987 |
| EP | 0251583 A2 | 1/1988 |
| EP | 0260970 A2 | 3/1988 |
| EP | 0270704 A1 | 6/1988 |
| EP | 0340159 A1 | 11/1989 |
| EP | 0409364 A2 | 1/1991 |
| EP | 0574707 A1 | 12/1993 |
| EP | 0611557 A2 | 8/1994 |
| FR | 2054731 A5 | 5/1971 |
| FR | 2346591 A1 | 10/1977 |
| FR | 2622430 A1 | 5/1989 |
| FR | 2728779 | 7/1996 |
| GB | 2084468 A | 4/1982 |
| WO | 8809157 A1 | 12/1988 |
| WO | 8901767 A1 | 3/1989 |
| WO | 9204874 A1 | 4/1992 |
| WO | 9515726 | 6/1995 |
| WO | 9603086 | 2/1996 |
| WO | 9616612 | 6/1996 |
| WO | 97/03086 A1 | 1/1997 |

* cited by examiner

METHOD OF ANCHORING AUTOLOGOUS OR ARTIFICIAL TENDON GRAFTS IN BONE

CROSS-REFERENCE TO RELATED APPLICATIONS

This application is a divisional application of U.S. patent application Ser. No. 12/617,392 filed on Nov. 12, 2009, now U.S. Pat. No. 8,100,969, which is a divisional application of U.S. patent application Ser. No. 10/623,212 filed on Jul. 18, 2003, now U.S. Pat. No. 7,637,949, which is a divisional application of U.S. patent application Ser. No. 08/976,257 filed Nov. 21, 1997, now U.S. Pat. No. 6,616,694, which is a continuation-in-part of both U.S. patent application Ser. No. 08/887,580, filed Jul. 3, 1997 now abandoned, and of U.S. patent application Ser. No. 08/754,566, filed Nov. 21, 1996 now abandoned, the contents of which are incorporated herein by reference in their entireties.

BACKGROUND OF THE INVENTION

This invention pertains to surgical systems and, more particularly, apparatus and methods for attaching autologous or artificial tendon grafts to bone. The invention has application in, for example, repair of the anterior cruciate ligament (ACL) of the knee. It may also be used, for example, for repair of other ligaments, such as of the elbow or ankle.

It is not uncommon for ligaments and other soft tissue to tear or detach from bone. Athletes, for example, often suffer tears or other injuries to the anterior cruciate ligament, one of the ligaments connecting the femur. (thigh bone) and the tibia (shin bone) at the center of the knee joint. The ACL, which limits hyperextension of the knee and prevents the backward sliding of the femur on the tibial plateau, may be injured when the knee is twisted beyond the normal range of motion, e.g., when the knee is twisted while bending and weaving during skiing and other sports activities. ACL injuries may take the form of total or partial tears.

Reconstruction is the most common form of surgery for injuries to the ACL and involves replacing the ACL with a graft of autologous or artificial tendon. An autologous tendon graft may be "harvested" from the patient's patellar ligament, which is part of the common tendon of the quadriceps femoris, connecting the patella to the tibia. An alternative autologous tendon graft may be harvested from the semitendinosus tendon, which runs posteriorly and medially along the thigh and which connects the upper femur to the tibia.

Traditionally, patellar grafts are harvested with attached bone plugs that can be securely fixed at the ends of a bone tunnel drilled through the tibia and femur using a metallic interference screw, a metal screw and washer, or buttons. Drawbacks associated with the use of the patellar tendon-include difficulties in harvesting the tendon and postoperative complications.

More recent success has been achieved using one or more strands of the triple-stranded semitendinosus, tendon, which can be harvested with minimal-post-operative complications. The strands can be used alone or in combination with the gracilis tendon, which anatomically runs parallel along the thigh to the semitendinosus tendon. Although semitendinosus tendons are increasingly used in ACL repair, they are difficult to attach to bone, due in part to the absence of associated bone plugs.

The art suggests, several techniques for attaching the semitendinosus tendon to bone in ACL repair. One such technique involves suturing the tendon to a button or staple on the exterior of the bone. Drawbacks associated with this method include stretching or failure of the suture, which may be subjected to tensile forces ranging from 30-50 pounds.

Another technique involves attaching a tendon graft to bone using metallic screws. Although such metal screws demonstrate stable fixation and good tensile strength, they have, a number of drawbacks. These include distortion of post-operative radiological studies, an allergic or rejection reaction resulting from metal sensitivity associated with permanently implanted metal screws, and the potential need for additional operations for removal or replacement.

Another technique involves attaching a tendon graft to an anchor affixed within a tunnel drilled in the bone. One anchor intended for this use is the Mitek Ligament Anchor available from Mitek Surgical Products, Inc. That anchor includes prongs that lodge into the bone after the anchor has been pulled into position by a suture. A drawback of that anchor is that it must be lodged in the cortical layer near the surface of the femur and therefore necessitates the use of long tendon segments. In addition, the anchor's design necessitates that it be fabricated from metal to ensure sufficient holding strength.

An object of this invention is to provide improved surgical systems, and more particularly, improved methods and apparatus for attaching autologous or artificial tendon grafts to bone.

Another object of this invention is to provide improved methods and apparatus for attachment of autologous or artificial tendon grafts (e.g., for ACL repair) that are in which the attachment means can be fabricated from polymers or bioabsorbable materials, without the use of metals.

A related object of this invention is to provide methods and apparatus for attachment of autologous and artificial tendons that minimize or eliminate the risk of graft pullout normally associated with ACL or other reconstructive orthopedic surgery.

SUMMARY OF THE INVENTION

The above objects are among those met by the invention, which provides improved methods and apparatus for attaching autologous or artificial tendon grafts to bone, e.g., during ligament and other reconstructive surgery, including ACL reconstruction. These allow anchoring the tendon graft in the bone, without metal and without placing undue load on sutures.

In one aspect, an assembly according to the invention comprises an insertion element and a stabilizing element. The stabilizing element has an outer surface adapted for interference fit with a bone hole. The insertion element includes an aperture through which a graft may be threaded or attached, and a stem adapted to be inserted into and retained in a cavity in the stabilizing element, e.g., by an interference fit. Additionally, the insertion element may comprise an aperture, slot, or barb, preferably at its distal end, to facilitate its insertion into the stabilizing element.

According to one aspect of the invention, the stabilizing element has a threaded outer surface that can be securely turned into the bone. In addition, the stabilizing element can have an inner bore that is smaller than the outer diameter of the insertion element, such that placement of the latter into the former causes the stabilizing element to deformably expand or otherwise obtain a still stronger pressure fit with the bone hole.

In another aspect, the invention provides a stabilizing element that has a flanged head that rests on the surface of the bone, outside of the bone hole, and that prevents the element from entering the bone hole beyond a certain point.

In further aspects of the invention, the insertion and stabilizing elements comprise bio-compatible materials. These avoid adverse biological reactions to the elements, as well as the need for a second surgical procedure to remove the elements.

A related aspect of the invention comprises a system comprising two or more anchoring assemblies as described above. Such a system can be used with one or more natural or artificial crafts to repair or strengthen a skeletal bone or joint. In ACL repair, for example, one stabilizing element: can be placed at one end of a bone hole drilled into the femur, and the other stabilizing element can be placed in an aligned tunnel drilled into the tibia. The first and second insertion elements can then be joined by the graft and inserted into their respective stabilizing elements. The stabilization element placed in the femur can be of the type having a threaded outer surface, while that emplaced in the tibia can be of the type having a flanged head. Such a configuration exploits the strong cancellous matter in the femur, which is well adapted to holding screw threads, and relies on the surface of the tibia to ensure a hold there.

Another aspect of the invention comprises a method for anchoring a graft in bone, for example for the replacement of a torn ligament. In this method, a tunnel or opening is drilled into the bone, and a stabilization element of the type described above is placed therein. A graft is looped through the head of an insertion element which, in turn, is inserted into the stabilization element. The insertion and stabilization elements may incorporate various structures designed to more effectively dispose and/or secure them in the bone tunnel, as described above. For example, the stabilization element may comprise a flanged head which prevents it from being pulled into the bone tunnel when tension is applied to the tissue graft after insertion of the insertion element.

In yet another aspect, the invention comprises a kit for securing a graft, e.g., for ACL replacement. The kit comprises two stabilization elements adapted to be secured in bone. These can include, for example, a stabilization element adapted to be secured (e.g., in the femur) by screw threads and a stabilization element adapted to be secured (e.g., in the tibia) by a flange which prevents the element from being pulled through a bone hole. The kit further comprises two insertion elements for securing the graft to the stabilization elements. Each insertion element is provided with an aperture at the head whereby an autologous or artificial tissue graft may be attached, as well as a stem adapted for insertion into a cavity in a stabilization element. These insertion elements may also comprise an aperture, slot, or barb, to facilitate their being pulled into the corresponding stabilizing element. The kit may optionally include a graft, such as a length of artificial tendon or a length of actual semitendinosus tendon.

More generally, the invention also comprises a kit for connecting two or more bones with grafts, for example, for replacing ligaments of the ankle or elbow. In this aspect, the kit comprises at least two stabilization elements of the types described above of appropriate size and anchoring configuration for the bones in which they are intended to be emplaced. The kit further comprises a comparable number of insertion elements of the types described above intended to be inserted into the stabilization elements, each of which comprises an aperture at the head suitable for affixing a graft. The kit may optionally include one or more lengths of artificial tissue, or it may be intended to be used with one or more autologous grafts.

Methods and apparatus of the instant invention overcome limitations of prior art systems for affixing grafts to bone. The two-piece apertured design enables construction of an anchor assembly to attach autologous or artificial tendon grafts securely within bone without the use of metal, and without placing the high loads on sutures that are associated with sewing or tying grafts directly to bone.

Yet other aspects of the invention comprise methods for ligament reconstruction, whereby various configurations of grafts are used to connect bone anchors of the types described above, or other anchors containing apertures suitable for threading grafts. These methods employ at least one graft having a filament extending from at least one of its ends. By way of example, this filament may be a suture which has been whip stitched to the end of a tendon graft.

The graft as emplaced according to this aspect of the invention may connect the bone anchors with two or four plies of graft material. In one two-ply configuration, a single graft is used. The graft is threaded through the aperture of one bone anchor, and folded to bring its ends into proximity. The two ends are then affixed to the other bone anchor, preferably by sewing with the attached filament(s). The anchors can be affixed in bone before or after threading of the grafts.

A related method, according to the invention also employs a single graft. The graft is threaded through the apertures in both bone anchors, and the attached filament(s) are used to connect the two ends of the graft to one another. This is preferably done by sewing the filaments at each end of the graft to the other end of the graft.

Another method according to the invention uses a single graft to connect two bone anchors via four plies of graft material, rather than by two plies as described in the previous two methods. According to this method, the graft (with at least one attached filament) is threaded through an aperture of a first bone anchor, and folded so that its ends are brought into proximity as described above. The two ends are then threaded through an aperture of a second bone anchor, and the graft is folded again, to bring its ends in contact with the first anchor. The attached filament(s) are used to connect the ends to the first anchor, preferably by sewing.

Other methods of attaching the grafts to bone anchors employ multiple grafts. These methods can lend additional strength to the reconstructed ligament. According to one such method, a graft with attached filament(s) is threaded through an aperture of one anchor and its ends are sewn to an aperture of another anchor, as described above. In addition, a second graft is threaded through the aperture of the anchor to which the first graft is sewn, and is sewn to the aperture of the anchor through which the first graft is threaded.

Another multiple-graft method of attachment threads two grafts (each with at least one attached filament) through the aperture of a bone anchor. The two grafts are folded, and their ends are attached to the aperture of a second bone anchor via the filaments. Each of these multiple-graft methods connects the anchors by four plies of graft material.

These and other aspects of the invention are evident in the drawings and in the description that follows.

BRIEF DESCRIPTION OF THE DRAWINGS

A more complete understanding of the invention may be attained by reference to the drawings, in which.

DETAILED DESCRIPTION OF THE INVENTION

Figure 1A:
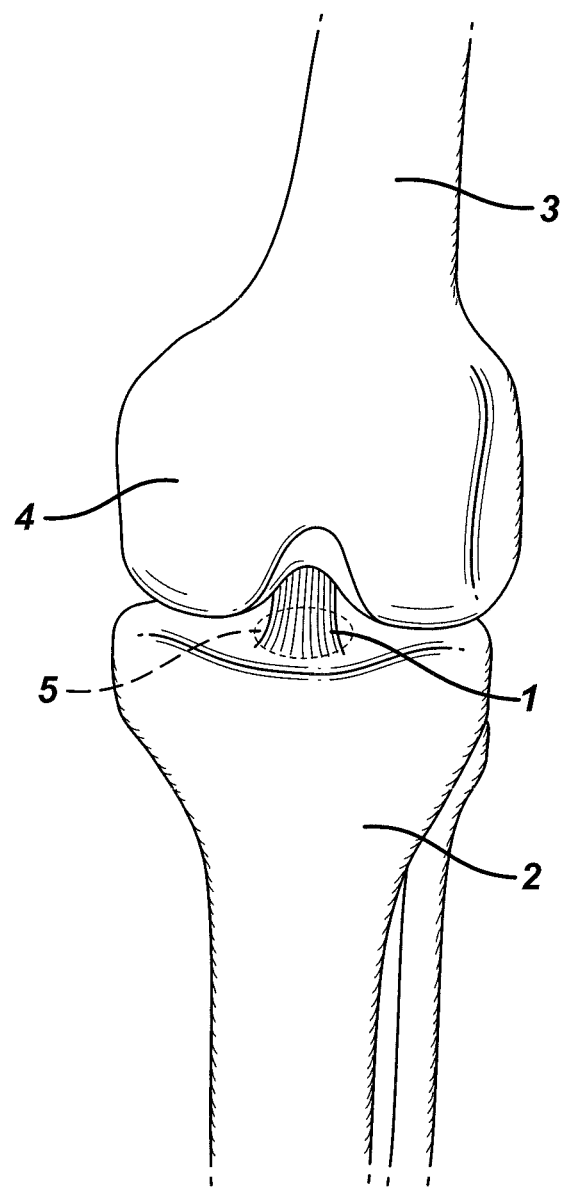
FIG. 1a depicts a frontal view of the bones of the knee and a partially torn anterior cruciate ligament (ACL)

FIG. 1a depicts a partially torn ligament of the knee, e.g., the anterior cruciate ligament (ACL) 1. In the illustration, the ACL is attached to a depression in the anterior intercondylar area (not shown) on the surface of the tibial plateau 5. This tibial attachment lies in front of the anterior intercondylar tubercle and is blended with the anterior extremity of the lateral meniscus (not shown). It passes upward, backward, and laterally to be fixed into the posterior part of the medial surface of the lateral condyle (not shown) of the femur 3. The tibia 2 and the patella 4 are also shown.

Figure 1B:
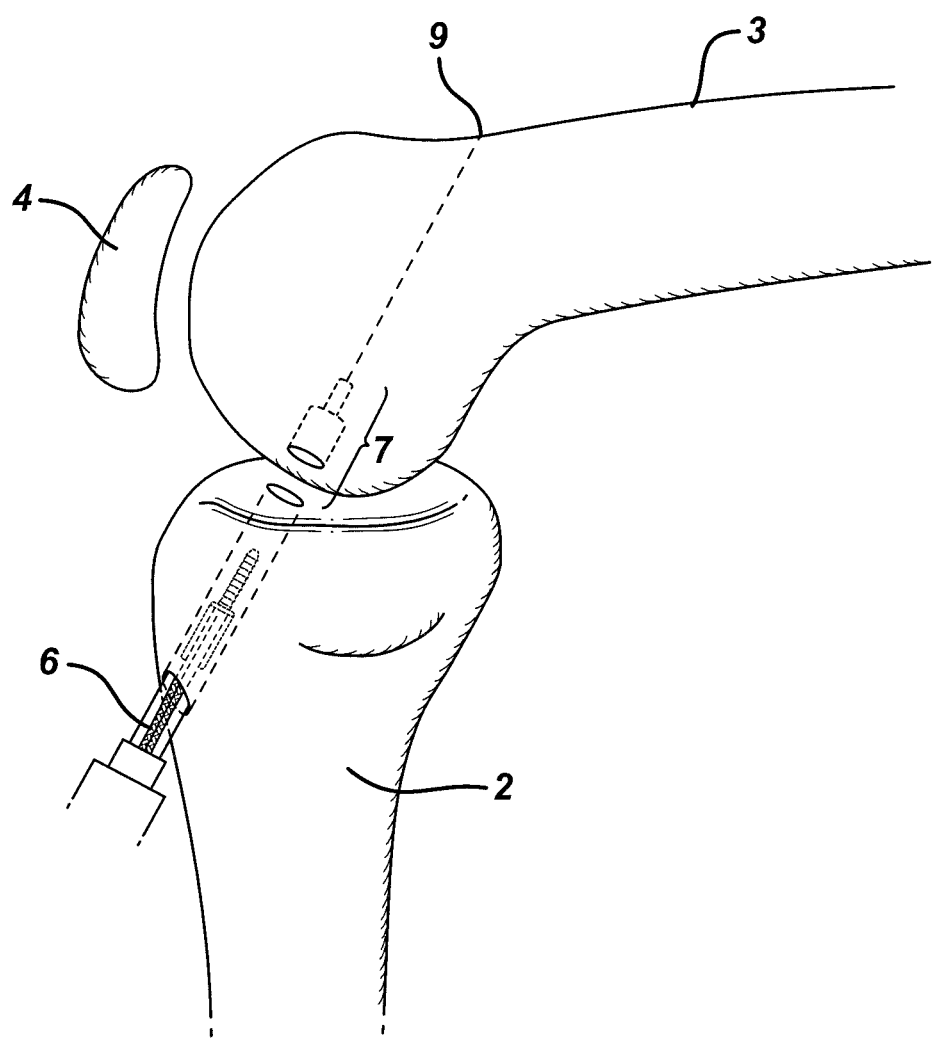
FIG. 1b depicts a side view of a method for creating a stepped tunnel through the tibia and partially through the femur for insertion of an anchor assembly according to the invention.

FIG. 1b depicts a method for creating a stepped tunnel 7 through the tibia 2 and partially through the femur 3 for insertion of an anchor assembly of the invention. In the illustration, a drill 6 is used by the surgeon to drill a tunnel beginning at the anterior surface of the tibia 2 and ending within the cancellous region of the femur 3. The drill tunnel 7 preferably will enter the femur 3 at or near the isometric point (not shown) close to the anatomical ACL attachment site in accordance with the prior art. The angle of the drill tunnel is in accord with that practiced in, the prior art for semitendinosus-style ACL repair. The stepped hole is formed by use of a stepped drill bit such that the ledge separating the wider and narrower diameter tunnels lies within the cancellous portion of the femur 3, e.g., within 10 mm to 70 mm within the femur of the posterior part of the medial surface of the lateral condyle and, preferably, within approximately 45 mm of that surface. The drill tunnel 7 may terminate within the cancellous portion of the femur 3, or, in the alternative, the surgeon may elect initially to fully penetrate the femur 3 with a guide wire (not shown), leaving a small exit aperture 9 on the opposing surface of the femur in accordance with the prior art covering ACL reconstructive surgery. It will be appreciated by those skilled in the art that the above-described invention is not limited to embedding an anchor assembly in the femur 3 but could also be practiced to embed an anchor in the tibia 2 or in bones comprising other joints, e.g., the ankle or elbow region, as well as in individual or groups of bones otherwise requiring repair or support.

Figure 2:
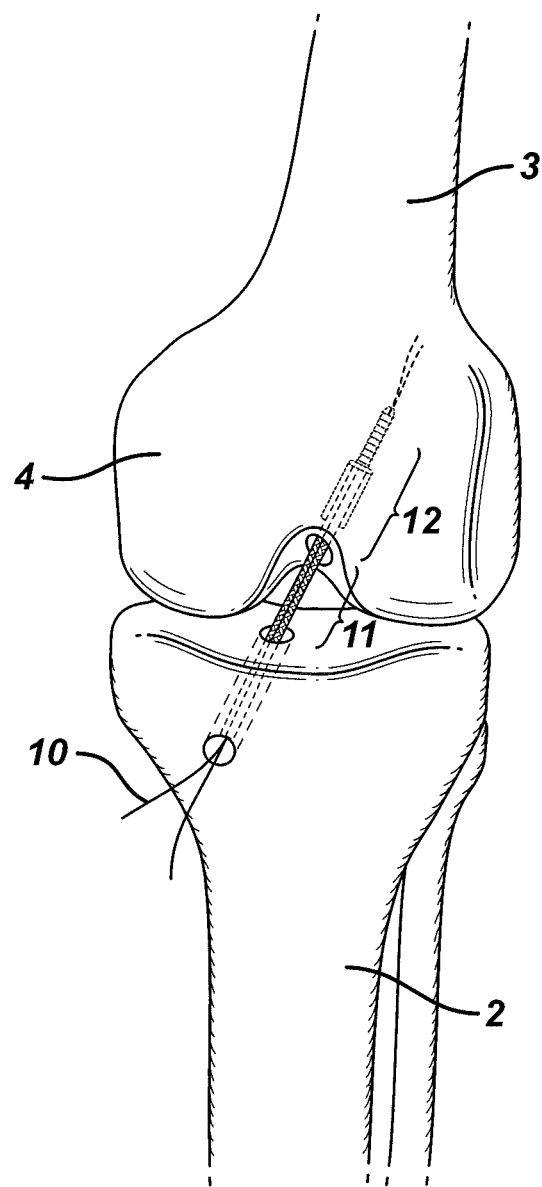
FIG. 2 depicts a frontal view of a method for affixing a tendon graft into the tunnel of FIG. 1b in accord with the invention.

FIG. 2 depicts shows a graft anchor assembly 12 of the instant invention embedded in bone, for example in the cancellous layer of the femur 3. A tendon graft 110 is looped through the aperture (see detailed drawing in FIG. 3) in an anchor assembly 12 with one or more free ends extending through other bone, for example, through the tibia 2.

Figure 3:
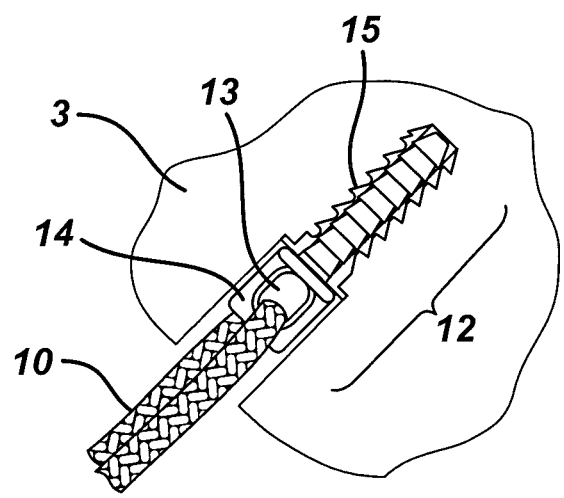
FIG. 3 depicts a detailed side view of an embedded anchor assembly of the present invention.
Figure 6:
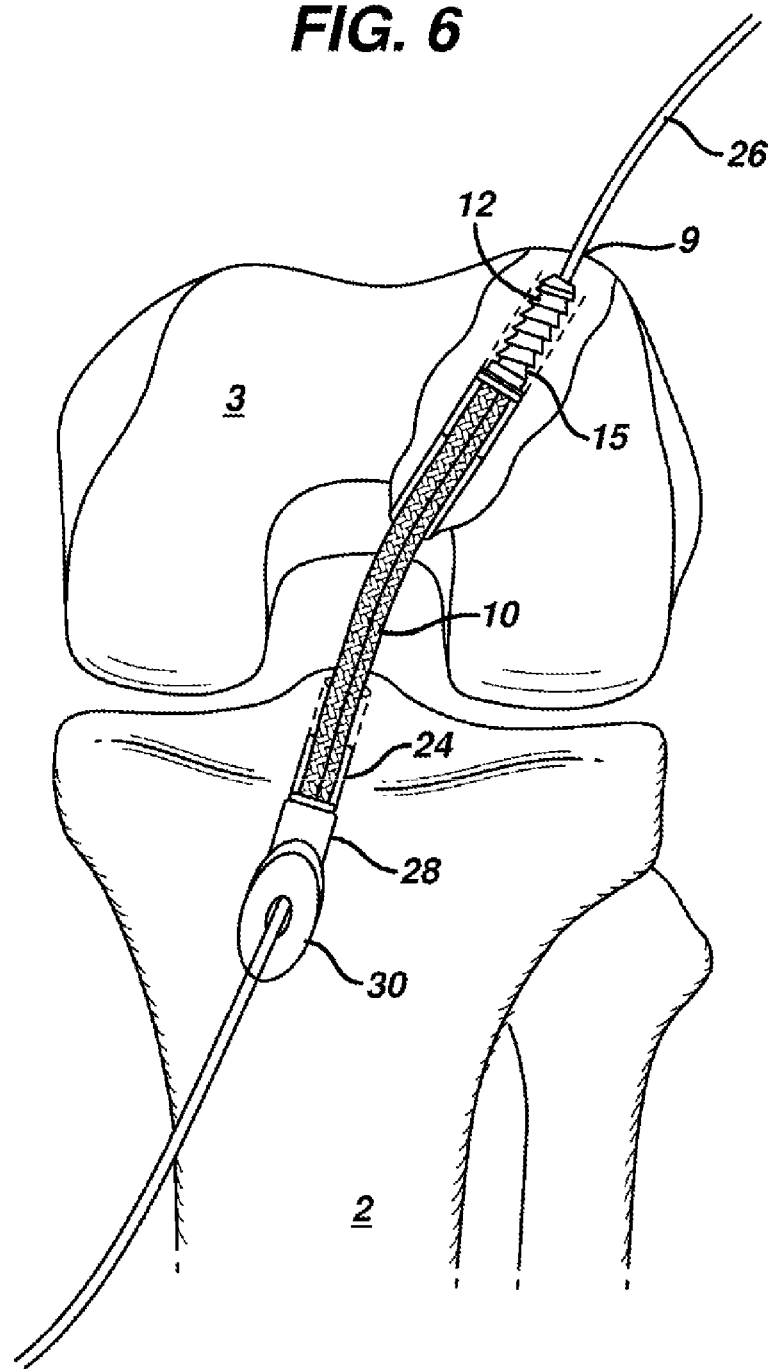
FIG. 6 depicts a detailed view of the insertion of an assembly according to yet another alternate embodiment of the present invention, this embodiment comprising the use of two stabilizing elements and two insertion elements.

FIG. 3 depicts in more detail an anchor assembly 12 in operating position embedded in the stepped bone tunnel. The autologous or artificial tendon graft 10 is looped through aperture 13 in the head of the insertion element 14. The stabilizing element 15 is embedded in the bone tunnel, for example by screwing into the stepped tunnel. In another embodiment, the stabilizing element may be secured by means of a flange which opposes tension on the tendon graft, as shown in FIG. 6. The insertion: element 14 is held in the stabilizing element 15 for example by compression fit, but could also be held by other interference fit, e.g., screwing (though, preferably by a thread) that requires twist, e.g., of lot more than 180.degree. (so as to avoid twisting the tendon) or by ratcheting or by other attachment mechanism for holding one element in another without excessive twisting.

Figures 4A, 4B, 4C, 4D:
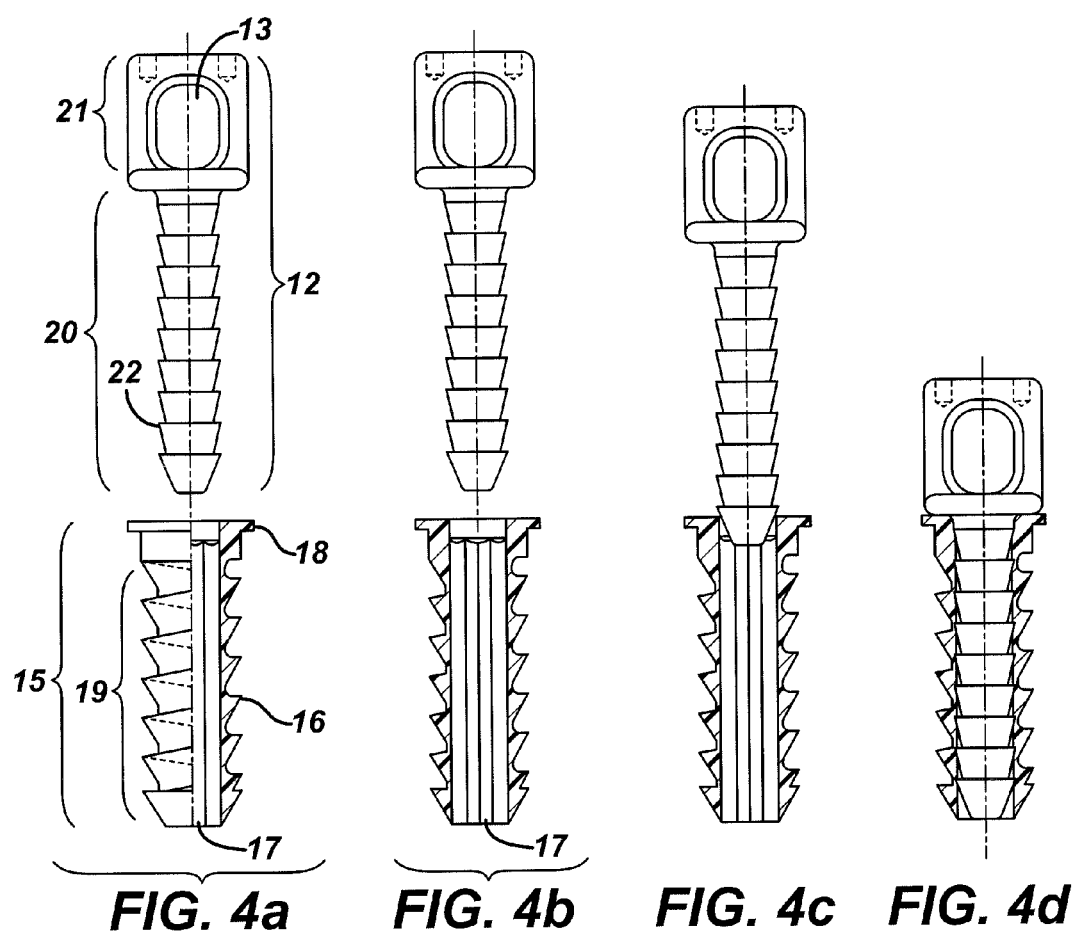
FIGS. 4a-d depict detailed views of an anchor assembly of the present invention.

FIGS. 4a-d depict the anchor assembly in detail. FIG. 4a depicts the stabilizing element 15 which comprises an elongated sleeve 19 containing external protrusions 16, for example, external threads. Stabilizing element 15 has a cavity 17; for example an elongated axial channel 17 extending at least partway from the proximal end of stabilizing element 15. For example, axial channel 17 could extend from the proximal to the distal end of stabilizing element 15. Stabilizing element has a flanged head 18. Stabilizing element 15 is comprised of a biocompatible material, for example, implant grade high density polyethylene, low density polyethylene (PE 6010 and PE 2030) and polypropylene (13R9A and 23M2) all made by Rexene, Dallas, Tex. or of a bioabsorbable material, for example poly-1-lactide or such as a lactide-glycolide composition. It may also be comprised of a metal, such as surgical implant grade steel.

FIG. 4a also depicts insertion element 14. Insertion element 14 has an aperture 13 containing head 21 for retaining a ligament replacement. Stem head 21 has an aperture 13 of a size suitable for receiving multiple strands of autologous and/or artificial tendon, but optimally for receiving two or more strands of semitendinosus tendon. The aperture 13 may have dimensions 0.10 inches-0.35 inches (height) by 0.05-0.30 inches (width), and, preferably approximately 0.220 inches by 0.160 inches. Insertion element 14 has a stem 20, for example an elongated stem 20. The stem has protrusions 22 extending outwardly: Stem, protrusions 22 may be inflexible. In the illustrated embodiment, the diameter of stem 20 has a larger outer diameter than the inner diameter of axial channel 17, such that stabilizing element 15 is capable of holding the insertion element 14 by compression fit upon insertion of the insertion element 14 into channel 17 of stabilizing element 15. The insertion element 12 can be tapped into the stabilizing, element 15 with an emplacement device (not shown). Alternatively, the insertion element can be configured to be screwed, ratcheted or placed in other interference fit within the stabilizing element. The insertion element 12 is comprised of a biocompatible material, for example implant grade high density polyethylene, low density polyethylene (PE 6010 and PE 2030) and polypropylene (13R9A and 23M2: all made by Rexene, Dallas, Tex.) or of a bioabsorbable material, for example poly-1-lactide or such as a lactide-glycolide composition, it may also be comprised of a metal, such as surgical implant grade steel.

FIG. 4b depicts axial channel 17 which has a non-cylindrical cross-section (not shown), optimally a polygon such as a hexagon Other non-cylindrical cross-sections such as a square or pentagon or even oval configurations are also envisioned. A non-cylindrical cross-section of the axial channel 17 is designed such that a emplacement device (not shown) such as a driver (not shown) with a corresponding non-cylindrical diameter can be inserted into a axial channel and turned such that the external threads 16 of the stabilizing element 15 are screwed into and grip the bone. One such driver is, e.g., an Allen wrench.

FIG. 4c depicts insertion of the distal end of an insertion element 12 into the axial channel 17 at the proximal end of a stabilizing element 15. The diameter of elongated stem 20 is slightly greater that the diameter of the non-cylindrical axial channel 17 of the stabilizing element. As a result as depicted in FIG. 4d, an elongated stem 20 of the insertion element 12 is held tightly in stabilizing element 15, for example by compression fit into stabilizing element 15 embedded in a stepped bone hole.

Figure 5A:
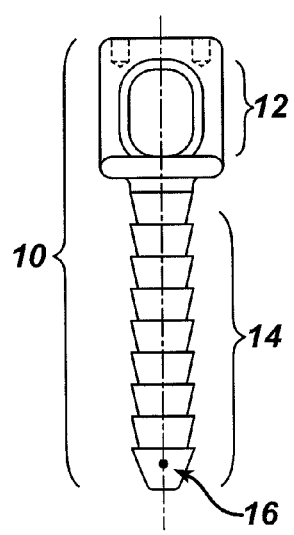
FIGS. 5a-5c depict detailed views of the insertion element of an anchor assembly according to an alternate embodiment of the present invention.

FIG. 5a depicts an insertion element 10 that can be pulled into the stabilizing element 15 (FIG. 4). As above, the insertion element 10 has an aperture 12 containing a head for retaining a ligament replacement—and a stem 14 with outwardly expanding protrusions. The diameter of stem is greater than the diameter of axial channel such that stabilizing element 15 is capable of holding the insertion element by compression fit upon insertion of the insertion element into the channel of the stabilizing element. Additionally, the insertion element 10 contains a structure, e.g., aperture 16, suitable for receiving a suture, a wire or other device that can be used to pull the element 10 into the stabilizing element 15 instead of, or in addition to, its being tapped into that element 15.

The aperture 16 or other such structure can be located at any point on the insertion element 10 but is preferably located at the distal end of the insertion element. Thus, for example, in an embodiment in which the stem of the insertion element is approximately 0.75 inches long with a diameter of 0.16 inches, the aperture is located 0.05-0.20 inches from the end of the insertion element and preferably 0.12 inches from the distal end.

Figure 5B:
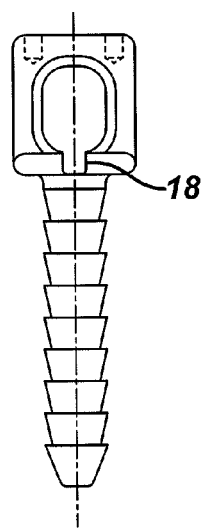
Figure 5C:
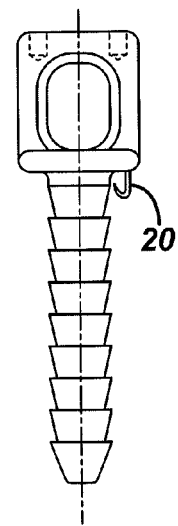

The aperture 16 (or other such structure) is sized sufficiently to accommodate a suture, wire or other pulling device. Those of ordinary skill in the art will of course appreciate that in lieu of an aperture, a slot, barb, hook (as shown in FIGS. 5b and 5c) or any other structure by which the insertion element can be pulled, can be utilized.

An anchor assembly incorporating an insertion element 10 of FIG. 5a is generally implanted as described above. In ACL reconstructive surgery, for example, a tunnel is drilled at the anterior surface of the tibia and ending within the cancellous region of the femur. The drill tunnel preferably enters the femur at or near the isometric point close to the anatomical ACL attachment site in accordance with the prior art. The angle of the drill tunnel is in accord with that practiced-in the prior art for semitendinosus-style ACL repair. A stepped hole is formed by use of a stepped drill bit such that the ledge separating the wider and narrower diameter tunnels lies within the cancellous portion of the femur, e.g., within at least 10 mm to 70 mm within the femur of the posterior part of the medical surface of the lateral condyle and, preferably, approximately 45 mm of that surface.

Although the drill tunnel may terminate within the cancellous portion of the femur, a guide wire or K-wire is preferably used to fully penetrate the femur, leaving a small exit aperture on the opposing surface on the femur. The stabilizing element is then embedded in the drilled bone tunnel, for example, by screwing it into the stepped tunnel. At this point, the K-wire (which is preferably equipped with an eyelet at its end) is used to thread a suture through the skin, bone and through the channel of the stabilizing element. The suture is then looped through the aperture, hook, barb, or slot, or other such structure in the insertion element. The insertion element is then pulled into the stabilizing element using that suture. Those skilled in the art will appreciate that a wire, hook or other such apparatus can be used in place of the aforementioned suture.

FIG. 6 depicts yet another embodiment of the invention, which employs two stabilizing elements and two insertion elements In this embodiment, a stepped tunnel is drilled in the bone, beginning at the anterior surface of the tibia 2 and ending within the cancellous region of the femur 3, similar to the tunnel depicted in FIG. 1b. The surgeon may elect initially to fully penetrate the femur 3 with a guide wire 26, leaving a small exit aperture 9 on the opposing surface of the femur in accordance with the prior art covering ACL reconstructive surgery.

Figure 7:
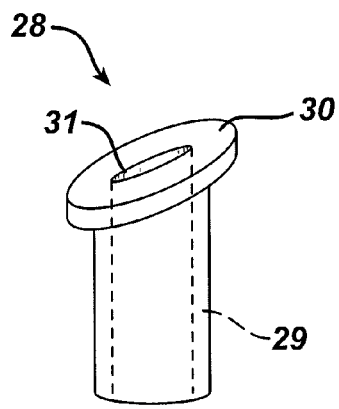
FIG. 7 depicts a detailed view of a stabilizing element comprising a flange.

A first stabilizing element 15 is then inserted in the femoral tunnel as has been described above. Insertion elements 12 and 24 are joined by a length of soft tissue 10, such as a tendon graft, and the first insertion element 12 is inserted into the stabilizing element 15, for example by pushing into the stabilizing element 15, or by pulling with a suture, wire, or other device 26 on a small aperture, slot, barb or hook on the insertion element 12. The second insertion element 24 is pushed into the bone tunnel, and then the second stabilizing element 28 is placed-in the bone tunnel. In the preferred embodiment depicted in FIG. 6, the second stabilizing element 28 comprises a flange 30 which limits the extent to which the stabilizing element can be pulled into the bone tunnel, e.g., by the tendon graft. This element is also depicted in FIG. 7 and is further discussed below. In other embodiments, the second stabilizing element may be secured by means of screw threads, an interference fit, or other methods known in the art. Finally, the second insertion element 24 is inserted into the second stabilizing element 28. In the preferred embodiment depicted in FIG. 6, the second insertion element is inserted into the second stabilizing element by pulling with a suture, wire, or other device 32 on a small aperture, slot, barb, or hook on the second insertion element 24.

In an embodiment for ACL replacement for an adult, the first stabilizing element is typically of a length 20 mm, an outer diameter of 8 mm, and an inner diameter of 3.5 mm. The first insertion element is typically of a length 40 mm and a diameter 8 mm. If the insertion element is equipped with an aperture whereby it may be pulled into the stabilizing element, that aperture has a typical diameter of 1 mm. The aperture for attachment of the tendon graft is typically about 5 mm.times.8 mm. The length of the tendon graft between the insertion elements is usually about 40 mm. Those skilled in the art will appreciate that the foregoing dimensions are supplied merely by way of example and that stabilization and insertion elements of sizes suited for other bones, joints and grafts can be used as well.

The surgeon can adjust the tension on the tendon graft by controlling the extent to which the insertion elements are inserted into the stabilizing elements. Insertion elements are typically designed so that full strength hold of the insertion element in the stabilizing element is obtained when the insertion element is inserted at least halfway into the stabilizing element. Thus, the depth of each insertion element is adjustable over a length of 10 mm for this preferred embodiment.

The second stabilizing element 28 of FIG. 6 is also illustrated in FIG. 7. This element comprises an elongated body 29, having a channel 31 for receiving an insertion element. The stabilizing element also comprises a flange 30, which prevents the element from being pulled completely into the bone hole by tension on a graft attached to an insertion element deployed in channel 31 The flange 30 may be perpendicular to the elongated body 29, or may be at an oblique angle to the body 29, as depicted in FIG. 7 The flange 30 may also be contoured to correspond to the shape of the outer surface of the bone in which it is to be emplaced. The surgeon may also elect to countersink the bone tunnel, so that the outer surface of the emplaced flange 30 is flush with the surface of the surrounding bone. In this embodiment, it may be desirable for the flange 30 to be tapered, having a thicker cross-section at the intersection of the flange 30 with the body 29 than at the outer edge of the flange 30.

When this embodiment is used in ACL repair as depicted in FIG. 6, the second stabilizing element has a typical length of 15 mm, an outer diameter of 8 mm, and an inner diameter of 3.5 mm. The flange has a typical outer diameter of 12 mm, and a typical thickness of 1 mm. The second insertion element has a length 40 mm and a diameter 8 mm. If the second insertion element is equipped with an aperture whereby it may be pulled into the stabilizing element, that aperture has a typical diameter of 1 mm. The aperture for attachment of the tendon graft is typically about 5 mm.times.8 mm. Those skilled in the art will appreciate that the foregoing dimensions are supplied merely by way of example and that stabilization and insertion elements of sizes suited for other bones, joints and grafts can be used as well.

The second insertion element and second stabilizing element, like the first elements, are comprised of a biocompatible material, for example implant grade high density polyethylene, low density polyethylene (PE 6010 and PE 2030) and polypropylene (13R9A and 23M2) all made by Rexene, Dallas, Tex. or of a bioabsorbable material, for example poly-1-lactide or such as a lactide-glycolide composition. These elements may also be comprised of a metal, such as surgical implant grade steel.

It will be apparent to those skilled in the art that the above-described invention is not limited to connecting the femur and tibia in an ACL reconstructive procedure, but could also be practiced to support or repair any bone or pair of bones with a length of soft tissue, e.g., in the ankle or elbow region.

Figure 8:
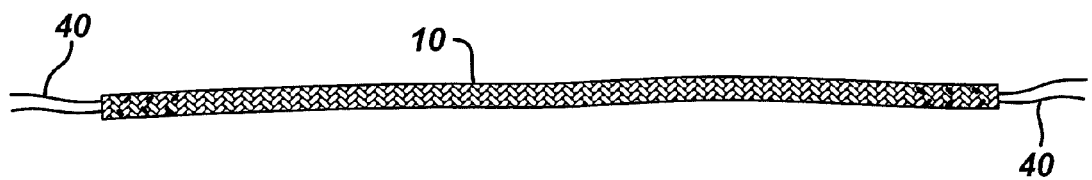
FIG. 8 depicts a detailed view of a graft prepared for attachment to one or more bone anchors.

The invention further comprises methods for connecting at least two bone anchors, for example those described above, with one or more lengths of graft material. FIG. 8 shows a graft 10 prepared according to a preferred embodiment of this aspect. The graft 10 may be an autologous tendon graft such as a length of semitendonosis or gracillis tendon, or an artificial graft. The graft 10 has a filament 40 (such as a suture) attached to at least one of its ends. In the preferred embodiment illustrated in FIG. 8, a suture 40 is whip-stitched to each end of the graft.

The anchors may be connected with one or with multiple grafts, in either a two-ply or four-ply configuration. Some configurations according to the invention are illustrated in FIGS. 9a-9f In FIG. 9a, a single graft 10 is used to connect two anchors 42 and 44 in a two-ply configuration. A graft 10 prepared as illustrated in FIG. 8 is threaded through an aperture in one anchor 44, and then folded so that the two ends of the graft 10 can be tied and/or sewn to an aperture in the other anchor 42 using the filament 40.

Figure 9A:
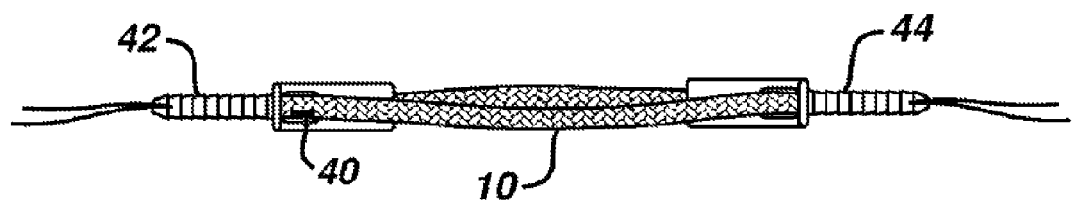
FIGS. 9a-9f depict detailed views of grafts linking two bone anchors according to the methods of the invention.
Figure 9B:
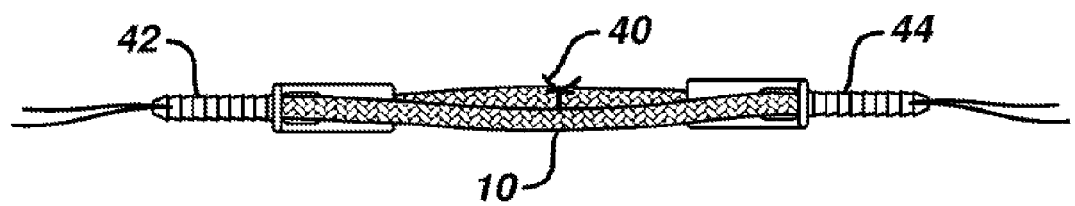

A related embodiment is illustrated in FIG. 9b. In this embodiment, the prepared graft 10 is threaded through apertures in each of the two anchors 42 and 44. The sutures 40 attached to the prepared graft are then tied, or, preferably, sewn, to connect the ends of the graft 10. This embodiment is also a two-ply arrangement.

Figure 9C:
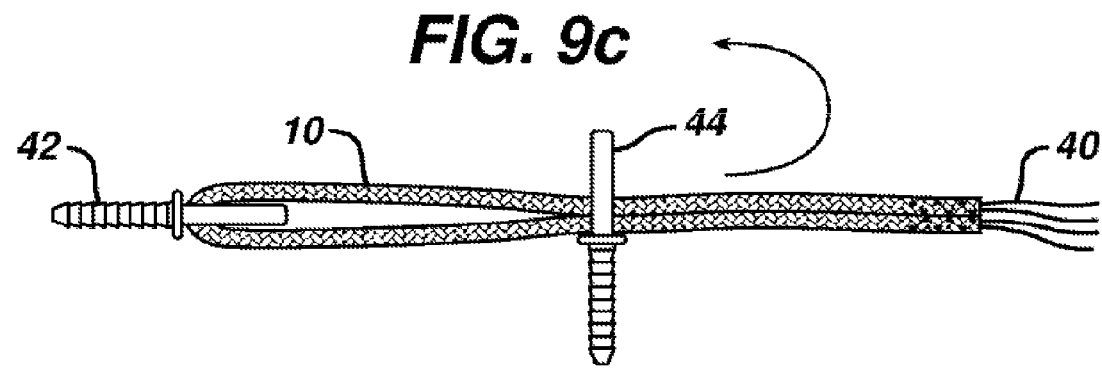
Figure 9D:
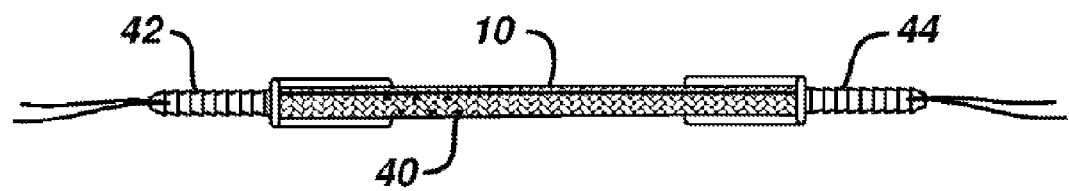

A four-ply connection between the anchors is achieved using a single graft in the embodiment illustrated in FIGS. 9c and 9d. A prepared graft 10 is first threaded through one anchor 42, and folded to bring the ends of the graft 10 into contact. These two ends are then threaded through the other bone anchor 44. FIG. 9c illustrates the configuration of the graft at this point in its emplacement. The graft 10 is then folded in half again, to bring the ends back to the first anchor 42, and the ends are sewn and/or tied there with the attached filaments 40, as illustrated in FIG. 9d, such that the four plies of graft material 10 now connect the bone anchors.

Figure 9E:
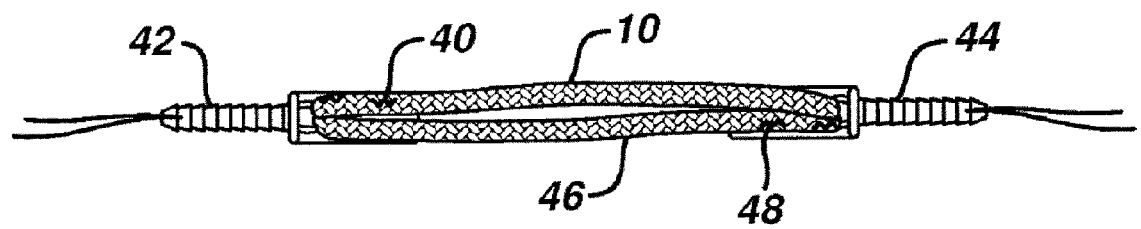
Figure 9F:
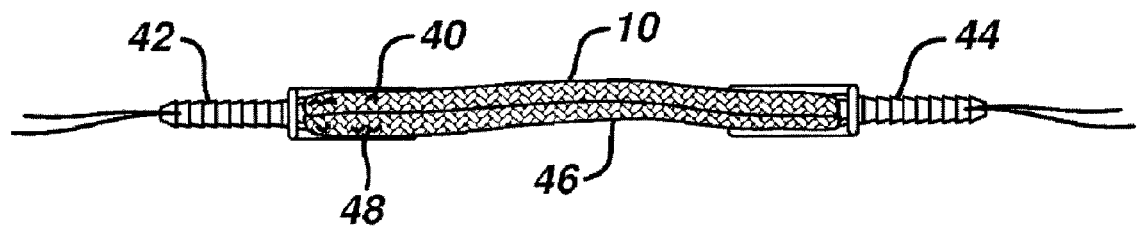

Other embodiments which achieve a four-ply connection between the anchors using multiple tendon grafts are illustrated in FIGS. 9e and 9f. In the first of these, one graft 10, prepared as shown in FIG. 8, is threaded through an aperture in a first anchor 44, and the sutures 40 at the end of the graft are sewn and/or tied to an aperture in a second anchor 42. A second graft 46 is then passed through the aperture in the second anchor 42, and sewn and/or tied to the aperture in the first anchor 44 with its attached sutures 48. In the second embodiment, illustrated in FIG. 9f, two grafts 10 and 46 are threaded through an aperture in the first anchor 44, and these two grafts are both sewn and/or tied to the aperture in the second anchor 42 with their attached sutures 40 and 48.

It will be apparent to one skilled in the art of ligament reconstruction that each of the embodiments illustrated in FIGS. 9a-9f has different strengths and that the preferred configuration for a particular use of the invention will depend on the ligament being replaced, the location and type of the bone anchors, and on whether the graft is attached to the anchors before or after they are affixed to the bone.

Described above are apparatus and methods meeting the objects set forth above. Those skilled in the art will appreciate that the illustrated embodiments are shown and described by way of example only, and that other, methods and apparatus incorporation modifications therein fall within the scope of the invention. For example, in addition to ACL reconstruction, the invention can be beneficially applied in connection with other soft tissue-to-bone attachments using bone tunnels, such as (by way of non-limiting example) repair of ligaments and tendons in other joints such as the elbow and ankle. In view of the foregoing.

The invention claimed is:

1. A method of ligament reconstruction comprising:
   (a) extending a filament from at least one end of a graft having at least two ends;
   (b) threading the graft through a first aperture in a first bone anchor;
   (c) threading the at least two ends of the graft through a second aperture in a second bone anchor;
   (d) using the filament to affix the at least two ends of the graft to the first aperture of the first bone anchor;
   (e) affixing the first bone anchor in bone; and
   (f) affixing the second bone anchor in bone.

2. The method of claim 1, wherein the first bone anchor is affixed in a femur and the second bone anchor is affixed in a tibia.

3. The method of claim 1, wherein the graft comprises at least one of an autologous tendon graft and an artificial tendon graft.

4. The method of claim 1, wherein affixing the first bone anchor in bone comprises inserting a stabilizing element having an axial channel extending therethrough into a bone opening and advancing an insertion element into the axial channel to deformably expand the stabilizing element, the insertion element having the first aperture formed therein.

5. The method of claim 4, further comprising adjusting a tension of the graft by controlling an extent to which the insertion element is advanced into the stabilizing element.

6. The method of claim 4, wherein advancing the insertion element comprises pulling a suture extending from a distal end of the insertion element to pull a distal end of the insertion element into a proximal end of the stabilizing element.

7. The method of claim 6, wherein the bone opening is drilled completely through a bone, the first stabilizing element is inserted into a first end of the bone opening, and the suture extends through and is pulled from a second end of the bone opening.

8. A method for anchoring a tissue graft within bone comprising:
   forming a first bone opening in a first bone;
   inserting a first stabilizing element into the first bone opening, the first stabilizing element comprising an elongated sleeve with an axial channel extending therethrough;
   forming a second bone opening in a second bone;
   inserting a second stabilizing element into the second bone opening, the second stabilizing element comprising an elongated sleeve with an axial channel extending therethrough;
   advancing a first insertion element into the axial channel of the first stabilizing element to deformably expand the first stabilizing element, the first insertion element having a first aperture formed therein through which a tissue graft having at least two ends is threaded;
   advancing a second insertion element into the axial channel of the second stabilizing element to deformably expand the second stabilizing element;
   threading the at least two ends of the tissue graft through a second aperture formed in the second insertion element; and
   affixing the at least two ends of the tissue graft to the first aperture of the first insertion element.

9. The method of claim 8, wherein the first bone is a femur and the second bone is a tibia.

10. The method of claim 8, wherein the tissue graft comprises at least one of an autologous tendon graft and an artificial tendon graft.

11. The method of claim 8, wherein at least one of the first and second bone openings is a stepped opening.

12. The method of claim 8, further comprising adjusting a tension of the tissue graft by at least one of controlling an extent to which the first insertion element is advanced into the first stabilizing element and controlling an extent to which the second insertion element is advanced into the second stabilizing element.

* * * * *